United States Patent [19]

Baron

[11] 4,379,453
[45] Apr. 12, 1983

[54] INFUSION SYSTEM WITH SELF-GENERATING PRESSURE ASSEMBLY

[76] Inventor: Howard C. Baron, 935 Park Ave., New York, N.Y. 10021

[21] Appl. No.: 186,955

[22] Filed: Sep. 15, 1980

Related U.S. Application Data

[63] Continuation-in-part of Ser. No. 543, Dec. 28, 1978, abandoned.

[51] Int. Cl.³ ............................................. A61M 5/00
[52] U.S. Cl. ..................................... 604/145; 222/95; 222/386.5
[58] Field of Search ........ 128/214 F, 214.2, DIG. 12, 128/225; 222/94, 95, 386.5, 399

[56] References Cited

U.S. PATENT DOCUMENTS

| | | | |
|---|---|---|---|
| 2,409,734 | 10/1946 | Bucher | 128/214 F |
| 2,628,615 | 2/1953 | Saftir | 128/216 |
| 2,690,179 | 9/1954 | Fox | 128/216 |
| 2,766,907 | 10/1956 | Wallace | 128/214 F X |
| 2,876,768 | 3/1959 | Schultz | 128/214 F |
| 3,023,750 | 3/1962 | Baron | 128/214 F |
| 3,153,414 | 10/1964 | Beall et al. | 128/DIG. 12 |
| 3,430,731 | 3/1969 | Satzinger | 222/386.5 X |
| 3,718,236 | 2/1973 | Reyner et al. | 222/386.5 |
| 4,048,994 | 9/1977 | Lo | 128/214 F |
| 4,090,514 | 5/1978 | Hinck et al. | 128/214 F |

*Primary Examiner*—Dalton L. Truluck
*Attorney, Agent, or Firm*—Schuyler, Banner, Birch, McKie and Beckett

[57] ABSTRACT

An infusion system with a self-generating pressure assembly includes a flexible infusion container which contains a fluid, such as blood and an expandible envelope which contains a pair of chemical agents which generate a gas when mixed. In use, the chemical agents are mixed by manual manipulation of the expandable envelope, creating a gas which expands causing the expandible envelope to bear against the flexible infusion container creating fluid pressure therein which causes the infusion fluid to flow out of the infusion container. The assembly may comprise a sleeve surrounding both the infusion container and expandable envelope, or a flexible panel secured to the side edges of the expandible envelope and forming a sleeve-like opening into which the infusion container is inserted.

19 Claims, 9 Drawing Figures

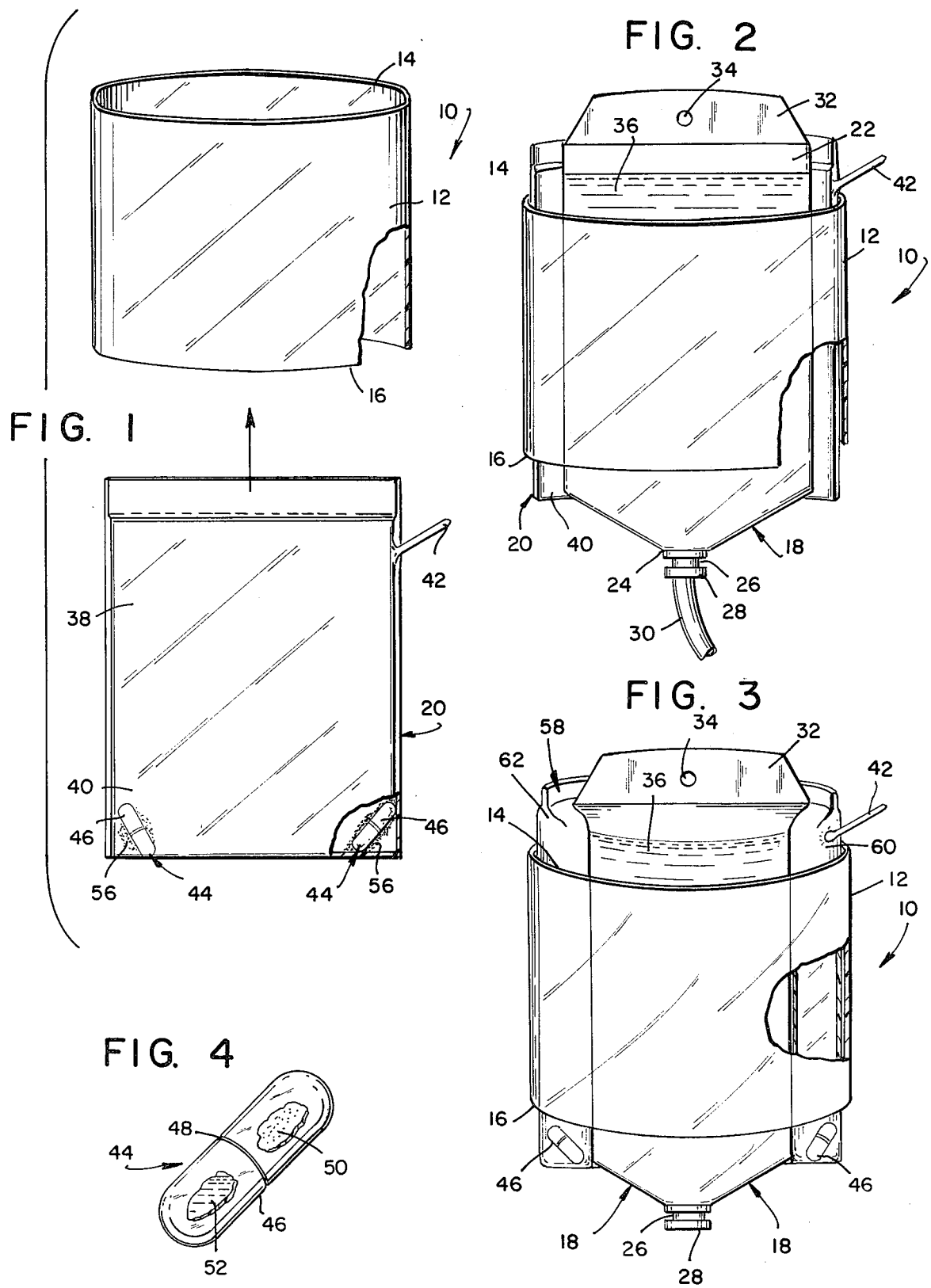

4,379,453

INFUSION SYSTEM WITH SELF-GENERATING PRESSURE ASSEMBLY

This application is a continuation-in-part of my co-pending U.S. patent application Ser. No. 543, filed Dec. 28, 1978 and entitled "Infusion System With Self-Generating Pressure Assembly", now abandoned.

BACKGROUND OF THE INVENTION

1. Field of the Invention

The present invention relates to infusion apparatus and more particularly to an infusion system having a self-generating pressure assembly.

2. DESCRIPTION OF THE PRIOR ART

The prior art related to the infusion of blood, plasma or other fluids into the blood stream includes conventional infusion systems in which a container containing the fluid is elevated, usually several feet above the patient, to permit the force of gravity to overcome the intravenous pressure. In order to avoid the inconveniences and other disadvantages of elevating the container, several techniques have been employed including the use of mechanical pumping equipment and manual manipulation of a soft plastic envelope containing the fluid to be infused. For example, U.S. Pats. Nos. 2,766,907 and 3,153,414 show pressure infusion apparatus in which an inflatable bladder is connected to an external source of pressure such as a gas tank or squeeze bulb. The use of mechanical pumping means, pressure tanks or other external pressure equipment requires a source of power and the procurement, maintenance and storage of a substantial quantity of mechanical equipment for use on a mass basis. Manual manipulation of a soft fluid container is objectionable on a mass basis because it requires the extensive use of medical or paramedical personnel. Another and even more serious objection to the use of these techniques is that extreme caution must be excercised when using these techniques in order to prevent the introduction of air into the patient's veins, causing an embolism.

Some but not all of the disadvantages of the prior art have been overcome by the device shown in my U.S. Pat. No. 3,023,750 entitled "Self-Generating Pressure Device for Infusion Administration Systems". The device shown therein comprises a flexible container which stores a supply of fluid to be fed intravenously, and a sealed flexible bag folded within the container. The flexible bag contains a supply of a dry chemical in powder form and a liquid chemical contained in a frangible capsule. In use, the frangible capsule is broken by manipulation of the flexible container and the two chemicals mix and react generating a gas which expands within the flexible bag. The flexible bag unfolds and exerts pressure on the fluid stored within the flexible container, forcing the fluid to flow through an injection system which has a length of tubing communicating with the flexible container and with an injection needle.

Although this device eliminates the need for elevating the fluid container to overcome the intravenous pressure, there remains a small but nevertheless significant danger of an embolus being created when the fluid is exhausted, or nearly exhausted, from the flexible container and the expanding flexible bag continues to exert a force which may pump air into the injection system. In addition, since the expanding flexible bag is located within the fluid container directly in contact with the fluid, any leakage of gas from the bag would contaminate the fluid and endanger the patient.

SUMMARY OF THE INVENTION

It is a major object of the present invention to provide an infusion system having a self-generating pressure device in which the infusion fluid does not come into contact with air or other gases and the danger of embolism is eliminated.

Another object of the present invention is to provide an infusion system having a self-generating pressure device comprising a transparent flexible plastic sleeve containing an expandable envelope and sized to receive a conventional flexible plastic infusion bag for compressing the latter to provide a pressure feed of the infusion fluid when the expandable envelope is inflated within the sleeve.

Still another object of the present invention is to provide an infusion system having a self-generating pressure device which is light in weight and which can be easily manufactured using mass production techniques resulting in a relatively low unit cost.

A further object of the invention is the provision of an infusion system of the character described consisting simply of a plastic sleeve and an expandable envelope which may be packed in flat compact form for shipment and storage, and which may be quickly and easily assembled with a standard filled infusion bag for use.

In accordance with the present invention, the infusion system comprises a flexible container which contains a flexible fluid bag and an expandable envelope. The fluid bag is filled with an infusion fluid and is located between the expandable envelope and a wall portion of the container, which is preferably in the form of a sleeve. A projecting portion of the expandable envelope contains a frangible member in the form of a capsule containing chemicals, which, when mixed, will generate gas within the envelope to inflate the latter. The capsule is secured at a fixed position and is accessible from the exterior of the container so that it may be grasped and squeezed through the walls of the expandible envelope to rupture the same and cause the chemical to mix for generating gas. The expandable envelope comprises locating means denoting the position of the capsule (such as a transparent wall portion) so that it can be quickly and easily located. The expandable envelope in its initial flattened form occupies only a minor portion of the interior of the container sleeve, but when it is inflated, it occupies a major portion of the interior of the sleeve and compresses the infusion bag against the wall portion of the sleeve to cause a flow of the fluid from the infusion bag to the patient receiving the infusion. The said wall portion of the sleeve is made of a height sufficient to overlie the infusion bag over substantially the entire length thereof.

Another object of the invention is to provide an infusion system having a self-generating pressure device wherein pressurization can be quickly initiated.

Another object of the invention is to provide an infusion system having a self-generating pressure device which can effect a variable and controlled rate of infusion.

The expandible envelope may be made of a size to fit within the sleeve behind the fluid bag so as to apply pressure on the rear wall thereof when the envelope is inflated. In another embodiment, the expandible envelope is made wide and is placed in folded condition within the sleeve in such a manner that when the envelope is inflated it embraces the fluid bag and its folded side portions apply pressure upon the sides of the bag.

The expandable envelope may be made separate from the sleeve, so that it is inserted together with the fluid bag into the sleeve when the system is to be used. In another embodiment, the expandable envelope is made integral with one wall of the sleeve.

The flexible container sleeve, the fluid bag, and the expandable envelope are each fabricated of a flexible transparent plastic using conventional heat sealing techniques resulting in a low unit cost and enabling the container to be disposable after a single use.

BRIEF DESCRIPTION OF THE DRAWINGS

Additional objects and advantages of the present invention will become apparent during the course of reading the following specification when taken in connection with the accompanying drawings, in which:

FIG. 1 is an exploded perspective view of an expandible envelope and an enclosure sleeve therefor, made in accordance with the present invention, with portions thereof shown broken away to reveal internal details of construction;

FIG. 2 is an elevational view showing the expandible envelope and a filled infusion bag mounted within the enclosure sleeve for use;

FIG. 3 is an elevational view similar to FIG. 2, but showing a modified form of expandible envelope mounted within the enclosure sleeve and embracing the infusion bag;

FIG. 4 is an enlarged view of the chemical-containing capsule used with the infusion system;

DETAILED DESCRIPTION

Figure 5:
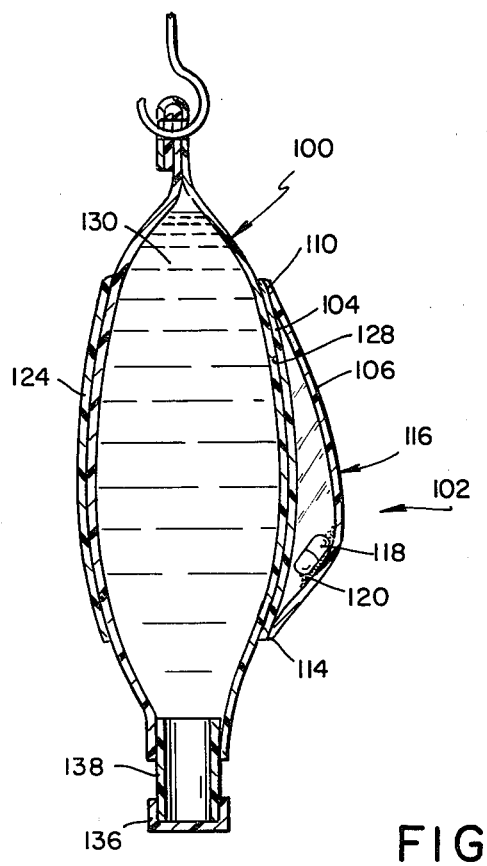
FIG. 5 is a longitudinal sectional view of an alternative embodiment of the invention.

Referring in detail to the drawings there is shown in FIGS. 1 through 4, by way of example, an infusion system 10 in accordance with the present invention, comprising a flexible transparent enclosure 12 in the form of a tubular sleeve made of a relatively soft and bendable plastic such as transparent polyvinyl chloride or the like. The sleeve 12 is normally stored in flat form, and has an open top end 14 and an open bottom 16.

The transparent sleeve 12 is sized to receive and enclose a fluid infusion bag 18 and an expandible envelope 20 containing means for generating gas in a sufficient volume to inflate said envelpe. The arrangement of these components is such that when the expandible envelope 20 is inflated, the fluid withing bag 18 is forced under pressure therefrom, in a manner to be presently described.

The infusion bag 18 is of the conventional and well-known type which is customarily used for infusion of blood, plasma, or other fluids to the body by gravity feed, and comprises a hollow bag body 22 made of a flexible transparent plastic material. The edges of the bag body 22 are completely sealed by a heat sealed margin except for an open neck portion 24 through which extends a hollow tube 26. The tube 26 communicates with the interior of the infusion bag 18, and its outer end is closed off by a sealing cap 28. When the infusion bag 18 is to be used, a flexible plastic tube 30 (FIG. 2) is inserted through the sealing cap 28 so as to communicate with the interior of the bag and receive fluid therefrom. The tube 30 terminates in the usual hollow needle (not shown) which is injected into the patient to receive the infusion.

At its top, the infusion bag 18 is formed with an integral flap 32 having a central opening 34 by means of which the infusion bag may be hung from a hook, stand, or other support. Ordinarily, the bag 18 would be hung in a vertical position well above the patient, so that the contained fluid may feed by gravity to the patient.

The infusion bag 18 is partially or fully filled with infusion fluid 36 to be administered. The fluid may be blood, plasma, or blood mixed with an anti-coagulent, etc. Prior to sealing the infusion bag body 22, the air is evacuated leaving a vacuum in the space above the fluid.

The expandible envelope 20 is transparent and is preferably made of the same soft and bendable plastic material as the sleeve 12, such as transparent polyvinyl chloride. In the embodiment of the invention shown in FIGS. 1 and 2, the envelope 20 is made of a width equal to or approximately equal to the width of the sleeve 12. The height of the envelope 20 is, however, appreciably greater than the height of the sleeve 12. When the envelope 20 is inserted into the sleeve 12 it fits easily therewithin, and its upper portion 38 and lower portion 40 project above and below the top and bottom edges 14, 16 of sleeve 12, as shown in FIG. 2. The envelope 20 is completely sealed around all of its edges, and has a hollow integral nipple 42 formed at the upper portion 38 thereof, and projecting therefrom. The nipple 42 is completely sealed and communicates with the interior of the envelope 20. When the envelope 20 is inserted within the sleeve 12, the nipple 42 is located above the top edge 14 of the sleeve 12 and is accessible for cutting for a purpose to be presently explained.

The envelope 20 contains gas generation means 44 which is operable to inflate and expand the envelope 20 while the latter is contained within the sleeve 12. The gas generation means 44 is mounted within the lower portion 40 of the envelope 20, so that it is located below the lower edge 16 of sleeve 20 is readily accessible to the user for actuation to generate gas within envelope 20.

The gas generation means 44 may consist of a container of compressed gas which can be opened or ruptured to release gas within the folded envelope, or more preferably it may comprise a store of two or more chemicals which, when mixed, generate gas. The expandible envelope 20, illustrated by way of example, contains at least one thin-walled capsule 46 or ampoule which may be ruptured or cushed to release and mix two chemical agents stored therein. The capsule 46 is shown in detail in FIG. 4 and comprises an elongated thin-walled capsule body of conventional shape, having an integral transverse partition wall 48 at or near its center, this partition wall also being thin and capable of being easily ruptured when the capsule 46 is squeezed and crushed. At one side of the partition wall 48, the capsule 46 contains a measured supply of powdered chemical 50, and at the other side of partition wall 48 the capsule contains a supply of liquid 52 which will react with the powdered chemical 50 to generate gas. Examples of suitable pairs of chemical agents for producing gas when mixed have been presented in the aforementioned U.S. Pat. No. 3,023,750. These examples include a measured amount of baking soda in dry powder form stored in one compartment of the capsule 46 and a supply of water stored in the other compartment of the capsule and separated by the partition wall 48. When the capsule 46 and its partition wall 48 are ruptured, the water mixes with the baking soda generating carbon dioxide gas. As another example, the capsule 46 may contain a supply of calcium carbonate separated from a supply of dilute hydrochloric acid.

The sleeve 12 and expandable envelope 20 of the infusion system 10 are packed and packaged in flat form for distribution and storage. When it is desired to administer infusion fluid from a fluid bag of any standard type, the infusion system is quickly and easily assembled by inserting the expandable envelope 20 within the sleeve 12 and then inserting the filled infusion bag 18 within said sleeve. The fluid bag 18 is thus located between the expandable envelope 20 and a portion of the wall of sleeve 12, the top portions of the infusion bag and the expandable envelope projecting above the wall of sleeve 12. Because the envelope 20 is transparent and the gas generation means 44 is located below the outer sleeve 12, the gas generation means may be instantly located by the user, and the capsule 46 is easily squeezed and ruptured.

When the capsule 46 is ruptured, its partition wall 48 is also ruptured, allowing the liluid 52 to mix with the powdered chemical 50, thereby generating gas which flows from the ruptured capsule 46 into the interior of the expandable envelope 20, and the latter begins to expand. As the envelope 20 expands, it bears against the fluid bag 18, pressing it against the adjacent wall portion of sleeve 12 and bulging out somewhat thereabove to lock the bag 18 against movement within said sleeve, so that the assembly may be lifted to a vertical position and hung up by inserting the bag aperture 34 on a hook or the like, without danger of the bag 18 slipping out of the sleeve 12. The hollow needle at the end of the tube 30 is inserted into the vein of the patient, and as the envelope continues to expand, it compresses the fluid bag 18 against the adjacent wall portion of the sleeve 12, creating pressure within the fluid bag 18 which forces its contained infusion fluid out through tube 30 and into the vein of the patient.

It will be noted that because the expandable envelope 20 is substantially the same height as the fluid bag 18, and the sleeve 12 is made of sufficient height to cover over the major portion of the fluid bag 18, the major portion of the fluid bag is squeezed between the expandible envelope 20 and the adjacent wall portion of the sleeve 12. Thus pressure is applied evenly to the fluid bag 18 along substantially the entire length thereof, and there is no tendency for the fluid bag to neck in and cut off the supply of its contained intraveneous fluid, as would be the possibility if a narrow sleeve were employed.

In accordance with the invention, the generated gas is always completely contained within the expandable envelope 20 and the infusion fluid 36 is contained within the fluid bag 18. The gas and the infusion fluid 36 can never come into contact, thus eliminating the danger of embolism. Even if the gas-filled envelope 20 should accidentally rupture, the released gas cannot mix with the infusion fluid 36 contained in the separate and sealed fluid bag 18.

Two identical capsules 46 may be contained within the expandible envelope 20, each immovably mounted in a lower corner of the envelope, as shown in FIG. 1. In emergency situations where a rapid flow of the infusion fluid is desired, both capsules may be ruptured to cause the expandable envelope 20 to inflate more quickly and thereby apply greater pressure upon the fluid bag 18. Where either one or two capsules are provided, each capsule 46 is secured to the lower portion 40 of the enevelope by a suitable adhesive 56. The capsule or capsules are therefore always located in an exposed position in which they may be instantly located and ruptured by the attendant who administers the infusion.

When the expandable envelope 20, in its flat, deflated condition, is originally inserted within the sleeve 12, it occupies only a minor portion of the interior space of said sleeve. When the envelope is inflated, it occupies a major portion of the interior space of the sleeve 12, until it finally presses the fluid bag 18 flat against the wall of said sleeve. FIG. 2 shows the expandable envelope 20 in an inflated condition behind the fluid bag 18.

If, for any reason, it becomes necessary to halt the pressure feeding of the infusion fluid to the patient, the pressure infusion system 10 may be instantly deactivated by merely cutting the nipple 42, as with a knife or scissors. This causes the gas within the expandible envelope 20 to escape to the atmosphere, so that the envelope becomes deflated. The infusion procedure may not proceed in the usual manner by gravity feed.

FIG. 3 shows a modified form of expandable envelope 58 which may be used in the infusion system 10. In this embodiment, the envelope 58 is made of a width appreciably greater than the width of the sleeve 12. The envelope 58 is thus inserted within the sleeve 12 with its side portions 60 and 62 folded inwardly and embracing the sides of the fluid bag 18. When the system is assembled and the envelope 58 inflated by rupturing one or both of the capsules 46, the main central body portion of the envelope 58 presses the fluid bag 18 against the wall of sleeve 12. At the same time, the inwardly-folded side portions 60 and 62 also inflate and press inwardly upon the sides of the fluid bag 18, so that the latter is compressed from rear to front, as well as at its sides. This insures pressure feeding of the entire liquid content of the infusion bag 18. In this embodiment, the capsules 46 are secured within the side portions 60 and 62 at the lower ends thereof, as shown in FIG. 3, in positions in which they are visible and readily accessible at all times.

In both embodiments previously described, after infusion of the fluid 36 in the fluid bag 18 is completed, the envelope 20 or 58 is deflated by cutting the nipple 42, and the deflated envelope and empty fluid bag removed from the sleeve 12 and discarded. A full fluid bag and a fresh deflated envelope containing capsules 46 may then be inserted in the sleeve 12 for the next infusion. Since the sleeve 12 is thus reusable, economy both in initial cost and in management of disposable material, is effected.

Figure 6:
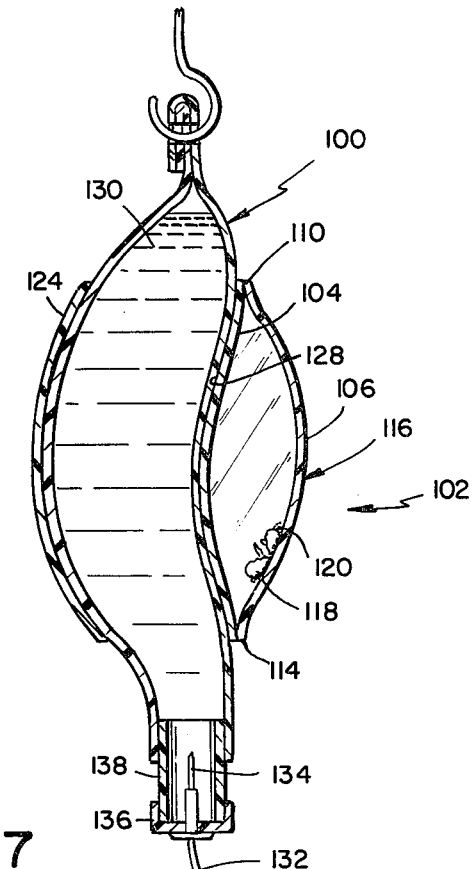
FIG. 6 is a longitudinal sectional view corresponding to FIG. 5, but showing the envelope containing the gas generating means partially expanded and showing a portion of the administration assembly in place.
Figure 7:
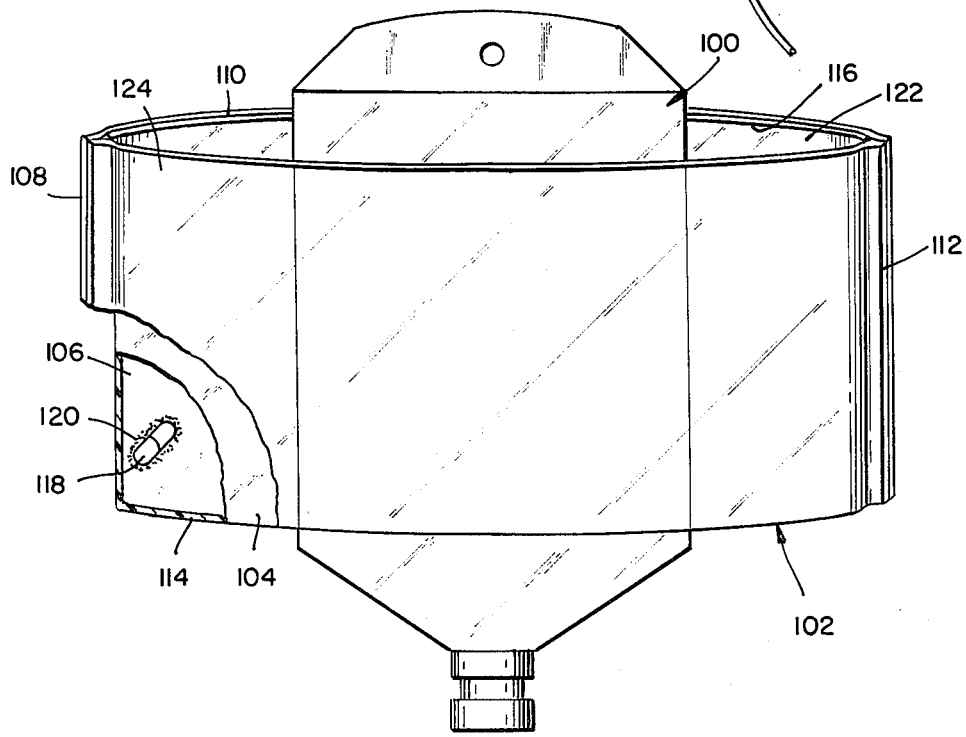
FIG. 7 is a perspective view of the device of FIG. 5 with portions thereof shown broken away to reveal internal details of construction.

FIGS. 5 to 7 illustrate still another embodiment of the invention in which the container of the infusion system is so constructed as to permit a pre-filled conventional flexible plastic infusion bag 100 to be quickly and easily inserted therein for the application of pressure on the infusion bag. In this embodiment, the envelope containing the gas generating means is an integral part of the flexible container for the conventional infusion bag 100.

In FIGS. 5-7, it will be seen that the container 102 includes a pair of walls 104, 106 which are joined by heat sealing around all of their marginal edges 108, 110, 112 and 114 to form a sealed envelope 116 which contains gas generating means.

The gas generating means, as previously described, may consist of a container of compressed gas which can be opened or ruptured to release gas within the envelope 116 or, more preferably, it may comprise a store of two or more chemicals which, when mixed, generate gas. In the latter instance, the envelope 116 contains one or two thin-walled capsules 118 or the type shown in FIG. 4, which contain the chemicals and which may be ruptured or crushed to release the chemicals and cause them to mix and generate gas within the envelope 116. The capsules 118 are preferably secured by cement 120 within the transparent envelope 116.

A wall of panel 124 is secured, as by heat sealing, to edges 108 and 112 of the envelope 116 forming a sleeve-like opening 122 between the inner surface of the wall 124 and the outer surface 128 of the wall 104 of the sealed envelope 116. The wall or panel 124 is of approximately the same length and width as the walls 104 and 106 of the sealed envelope 116, and because of the flexibility of these walls, the sleeve-like opening between the wall of panel 124 and the sealed envelope 116 may be expanded to permit a pre-filled conventiona infusion bag 100 to be inserted therethrough to the contained position shown in FIGS. 5-7. In this contained position, the filled infusion bag 100 is embraced between the sealed envelope 116 and the wall or panel 124.

The walls 104, 106, 124 may be formed of one of a number of plastic film materials. More preferably, walls 106 and 124 are formed of a flexible film and wall 104 is formed of a stretchable film so that the major portion of the expansion of the envelope 116 is directed toward the inserted infusion bag 100, thereby applying pressure to the fluid 130 contained in the infusion bag 100.

In use, the conventional flexible infusion bag 100 is placed between the walls 104 and 124. A flexible plastic tube 132 is connected to the bag 100, in communication therewith, by inserting a hollow needle 134 through a rubber cap 136 covering over a tube 138 secured within the bottom of fluid bag 100. A hollow needle (not shown) at the opposite end of the tube 132 is injected into the patient to receive the infusion. The capsule 118 is now ruptured, in the manner previously described, by manipulation from outside the envelope 116, causing the two chemical agents therein to mix and generate a gas which expands the envelope 116 as is shown in FIG. 6. The expanding envelope 116 bears against the contained infusion bag 110, squeezing the infusion bag 100 against the wall or panel 124 and creating pressure within the infusion bag 100 which forces its contained fluid 130 out through the tube 132 and into the vein of a patient.

As shown in FIG. 7, the container device 102 is made relatively wide, so that standard infusion bags containing 1,000 cubic centimeters of fluid as well as standard infusion bags containing 500 cubic centimeters of fluid may be easily inserted in the sleeve-like opening between the walls 104 and 124. As in the previous embodiment, the height of the walls 104 and 128 are sufficient to cover over the major extent of the front and rear walls of the infusion bag 100 to insure even pressure over the height of said infusion bag.

Figure 8:
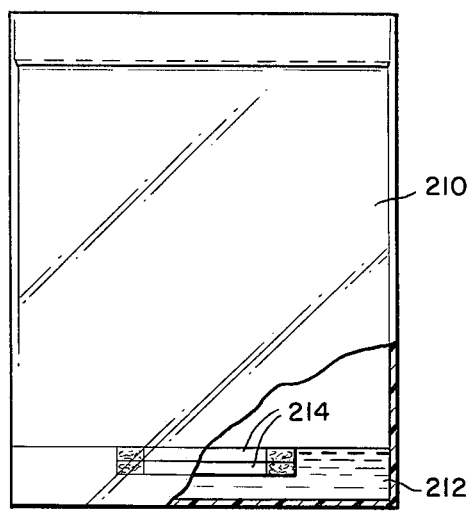
FIG. 8 is an elevational of the expandible envelope, with a portion broken away, showing a modification of the pressure generating assembly.
Figure 9:
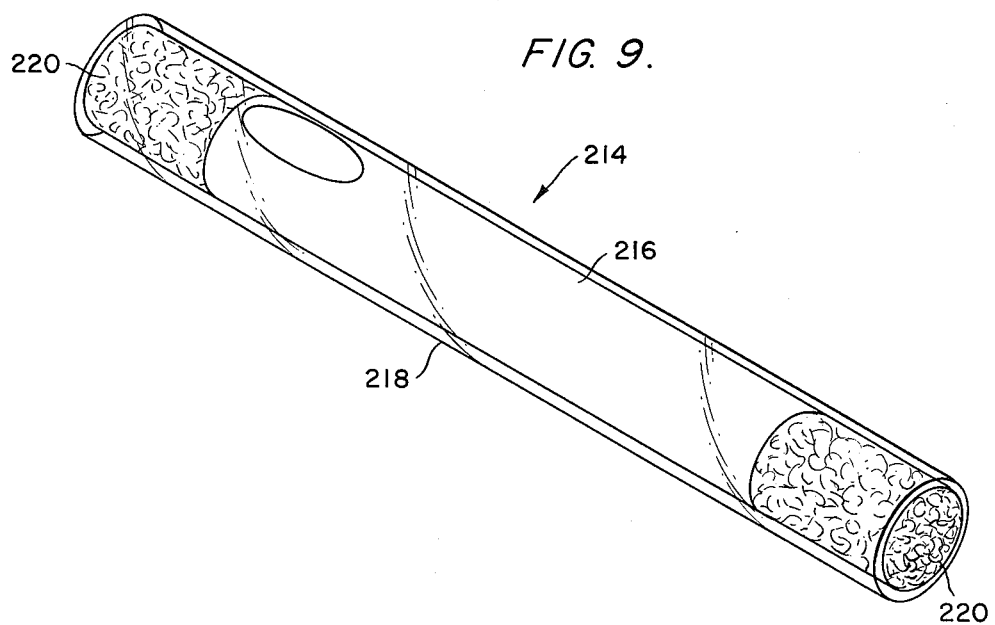
FIG. 9 is a perspective view of a portion of the modified pressure generating assembly shown in FIG. 8.

FIGS. 8 and 9 illustrate a modification of the pressure generating assembly, which can be incorporated into any of the above described embodiments of the invention. In this modification expandible envelope 210 contains a small measured quantity (for example 50 cc) of sodium bicarbonate solution 212. Placed loosely within expandable envelope 210 are two commercially available capsules 214, each of which contains a measured quantity (for example 2.5 cc) of glacial acetic acid. Other suitable gas producing reagent solutions and substances may be placed within envelope 210 and capsules 214.

FIG. 9 illustrates the detailed construction of each capsule 214. The capsule contains a thin-walled glass ampoule 216, which contains a measured quantity of glacial acetic acid. Ampoule 216 fits closely within a flexible but tough, clear plastic tube 218. A cotton wad 220 closes off each end of plastic tube 218.

In use, a capsule 214 is grasped by the person administering the infusion fluid, and is squeezed or bent to break glass ampoule 216. Plastic tube 218 prevents the shards of glass from piercing the wall of expandible envelope 210. Cotton wads 220 prevent the glass from leaving tube 218, while permitting the passage and commingling of the glacial acetic acid and the sodium bicarbonate solution. The resulting chemical reaction generates gaseous carbon dioxide and sodium acetate. Sodium acetate is relatively innocuous and is readily disposed of without fear of causing environmental damage. Each ruptured capsule containing 2.5 cc of glacial acetic acid will yield a pressure of approximately 150 mm Hg. when reacted with the 50 cc of sodium bicarbonate solution (6 grams sodium bicarbonate in 50 cc water) contained within the expandible envelope.

For a normal slow infusion only one capsule 214 will be ruptured at first. When the infusion slows due to partial depletion of the infusion fluid, the second capsule 214 is ruptured to complete the infusion. Where a rapid infusion is required, both capsules 214 can be broken simultaneously to generate a pressure of some 300 mm Hg.

A light color dye may be incorporated in the sodium bicarbonate solution 212 within expandible envelope 210. Such a dye is useful for leak detection, and for ascertaining which acetic acid capsule 214 has been ruptured, inasmuch as the dyed solution will enter the ruptured capsule.

The embodiments of the invention shown herein make possible the use of a standard conventional infusion bag which is filled and sealed according to conventional procedures and protocols and provides the advantages of a self-generating pressure device which is provided entirely separately from the infusion bag to be subsequently used.

While preferred embodiments of the invention have been shown and described herein, it is obvious that numerous omissions, changes and additions may be made in such embodiments without departing from the spirit and scope of the invention.

I claim:

1. For use with a flexible-walled infusion bag storing a supply of fluid to be fed intravenously and having an outlet, an infusion system for dispensing fluid under pressure from said infusion bag comprising:

an outer container having a substantially inextensible wall portion defining an interior cavity sized for removably receiving said infusion bag therein;

an expandable envelope disposed within said cavity adjacent said infusion bag, said expandable envelope being completely sealed and having a normal collapsed condition in which it occupies a minor portion of said cavity; and manually operable inflation means within said expandible envelope including at least two separate frangible capsules, each of said capsules being independently rupturable only by manipulation through the wall of said expandible envelope to generate separate supplies of gas within said expandible envelope, when ruptured, to expand said envelope and squeeze said infusion bag against said inextensible wall portion, thereby dispensing said fluid from said infusion bag through said outlet.

2. An infusion system according to claim 1 wherein said expandable envelope contains a quantity of a first reagent, and each of said capsules contains a quantity of second reagent which reacts with said first reagent, when each of said capsules is ruptured, to generate an inflating gas.

3. An infusion system according to claim 2 wherein said first reagent is sodium bicarbonate solution, said second reagent is glacial acetic acid, and said inflating gas is carbon dioxide.

4. An infusion system according to claim 3 wherein said expandible envelope contains approximately 6 grams of sodium bicarbonate in 50 cc water, and each of said capsules contains approximately 2.5 cc glacial acetic acid.

5. An infusion system according to claim 2 wherein said expandible envelope and said outer container have transparent flexible walls to permit viewing of said inflation means.

6. An infusion system according to claim 5 wherein said first reagent contains an indicator dye which enters each ruptured capsule to indicate its ruptured condition.

7. An infusion system according to claim 1 wherein said capsules are fixedly positioned at discrete locations within said expandible envelope.

8. An infusion system according to claim 1 wherein each of said capsules comprises a frangible glass ampoule housed within an open-ended protective plastic tube, and porous wadding material retained in the ends of each tube.

9. For use with a flexible-walled infusion bag storing a supply of fluid to be fed intravenously and having an outlet, a disposable infusion system for dispensing fluid under pressure from said infusion bag comprising:

an outer container having a tubular sleeve with an open top and bottom end, an interior space sized for removably receiving said infusion bag therein, and a continuous, unbroken wall including an inextensible wall portion, an expandible envelope disposed within said container at one side of said interior space and opposite to said inextensible wall portion of said container;

said infusion bag being receivable within said interior space between said expandible envelope and said wall portion;

said container wall having a height sufficient to extend over the major portion of said infusion bag when the latter is received within said container, with at least a portion of the expandable envelope projecting beyond said container wall;

said expandible envelope having flexible walls, the envelope being completely sealed, and having a normal collapsed condition in which said expandible envelope occupies a minor portion of the interior space of said container; and means including a frangible member secured at a fixed position within the projecting portion of said expandible envelope for generating a supply of gas therein in sufficient volume to cause said expandible envelope to expand to an extended position in which it substantially fills the interior space of said container, the projecting portion of said expandible envelope comprising locating means for denoting the position of said frangible member so that said frangible member is readily accessible from the exterior of said container through the projecting portion of said flexible wall of said expandible envelope, whereby said frangible member may be quickly and easily located and manually ruptured to generate gas within said expandible envelope, thereby causing said expandible envelope to expand to press said infusion bag against said wall portion of said container to lock said infusion bag in position and create pressure within said infusion bag sufficient to cause a flow of said fluid from said infusion bag through the outlet thereof.

10. An infusion system according to claim 9 in which said expandible envelope is formed integrally with said tubular sleeve.

11. An infusion system according to claim 9 in which said expandible envelope is formed separately from said tubular sleeve and is sized for insertion therein.

12. An infusion system according to claim 11 in which said expandible envelope has a width substantially equal to the width of said tubuar sleeve.

13. An infusion system according to claim 11 in which said expandible envelope has a width greater than the width of said tubular sleeve, said envelope being insertible into said sleeve with its side portions folded inwardly and embracing said infusion bag, whereby when said envelope is inflated, said folded side portions apply pressure against the sides of said infusion bag.

14. An infusion system according to claim 9 in which said frangible member is a capsule containing a plurality of chemical ingredients capable of generating gas when mixed, said frangible member having at least one thin partition wall separating said chemical ingredients.

15. An infusion system according to claim 14 in which said sleeve and expandible envelope are made of flexible, transparent plastic sheet material.

16. An infusion system according to claim 15 in which the upper and lower portions of said expandible envelope project beyond the upper and lower edges of said tubular sleeve.

17. An infusion system according to claim 16 in which said expandible envelope is formed with an integral nipple projecting from the upper portion thereof and communicating with the interior of said envelope.

18. A method of administering an infusion fluid to a patient through an intravenous infusion tube from a flexible-walled infusion bag installed in an infusion system comprising an outer container having a substantially inextensible wall portion defining an interior cavity in which said infusion bag is received, an expandible envelope disposed within said cavity adjacent said infusion bag, said expandible envelope being completely sealed and having a normal collapsed condition in which it occupies a minor portion of said cavity, and inflation means within said expandible envelope including at least two separate frangible capsules, each of said capsules being independently rupturable only by manipulation through the wall of said expandible envelope to generate separate supplies of gas within said expandible envelope, when ruptured, to expand said envelope and squeeze said infusion bag against said inextensible wall portion, thereby dispensing said fluid from said infusion bag through said infusion tube to the patient, comprising the steps of:

manually rupturing only one of said capsules by manipulating it through the wall of said expandible envelope to generate a first gas pressure which expands said envelope and dispenses a portion of the fluid from said infusion bag; and manually rupturing the second of said capsules by manipulating it through the wall of said expandible envelope when the flow of infusion fluid has slowed due to partial depletion of the fluid from said infusion bag and reduction in pressure within said expandible envelope, to generate a second gas pressure which further expands said envelope to complete dispensing of substantially all fluid remaining in said infusion bag.

19. An infusion system according to claim 9 wherein said locating means comprises a transparent wall portion of said expandible envelope at the location of said frangible member which exposes said frangible member to view.

* * * * *